(12) United States Patent
Hucklenbroich et al.

(10) Patent No.: US 7,214,508 B2
(45) Date of Patent: May 8, 2007

(54) METHOD FOR COARSE PURIFICATION OF CELL DIGESTS FROM MICROORGANISMS

(75) Inventors: Joerg Hucklenbroich, Remscheid (DE); Markus Mueller, Dormagen (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 10/504,258

(22) PCT Filed: Feb. 20, 2003

(86) PCT No.: PCT/EP03/01769

§ 371 (c)(1),
(2), (4) Date: Aug. 10, 2004

(87) PCT Pub. No.: WO03/070942

PCT Pub. Date: Aug. 28, 2003

(65) Prior Publication Data

US 2005/0089950 A1    Apr. 28, 2005

(30) Foreign Application Priority Data

Feb. 20, 2002   (DE) ............................... 102 07 170

(51) Int. Cl.
*C12P 1/00*     (2006.01)
*C12N 1/06*     (2006.01)
*C12N 1/08*     (2006.01)
*C12Q 1/68*     (2006.01)

(52) U.S. Cl. ..................... 435/41; 435/270; 435/6; 536/23.1

(58) Field of Classification Search ............... None
See application file for complete search history.

(56) References Cited

U.S. PATENT DOCUMENTS 6,120,985 A * 9/2000 Laugharn et al. ............ 435/1.3
6,218,531 B1   4/2001 Ekenberg ................ 536/25.41
2006/0166331 A1 * 7/2006 Au-Yeung et al. ......... 435/91.1

FOREIGN PATENT DOCUMENTS

EP        0 875 271 B1    11/1998

OTHER PUBLICATIONS

An, G., Hidaka, K., Siminovitch, L. 1982. Expression of Bacterial B-Galactosidase in Animal Cells. Molecular and Cellular Biology. 2(12):1628-1632.*
Reddy, K.J. and Gilman, M. 1993. Isolation of High-Quality RNA from Gram-Negative Bacteria in Preparation of Bacterial RNA. Current Protocols in Molecular Biology. Unit 4.4.*
Heilig, J.S., Eberling, K.L., and Brent, R. 1998. Preparation of Crude Lysate by Alkaline Lysis in Large-scale Preparation of Plasmid DNA. Unit 1.7.*
Itoh, M. et al. Automated filtration-based high throughput plasmid preparation system. Genome Research. 1999, vol. 9, p. 463-470.*
Atmospheric puressure article from Wikipedia, retrieved from http://en.wikipedia.org/wiki/Atmospheric_pressure.*
Itoh M et al. "Automated filtration-based high throughput plasmid preparation system", Genome Research, 1999, vol. 9, p. 463-470.*
Burns SE et al. "Microbubble generation for environmental and industrial separations", Separation and Purification Technology, 1997, bol. 11, p. 221-232.*
Conn, G.L. and Draper, D.E., "RNA Structure," *Current Opinion in Structural Biology*, Jun. 1998, 8(3):278-285.
Thomas, C.M., "Paradigms of Plasmid Organization," *Molecular Microbiology*, Aug. 2000, 37(3):485-491.

* cited by examiner

*Primary Examiner*—Gary Benzion
*Assistant Examiner*—Stephanie Mummert
(74) *Attorney, Agent, or Firm*—Seed IP Law Group PLLC

(57) ABSTRACT

The present invention relates to the coarse clarification of lysed cell material from microorganisms and particularly to a method of obtaining nucleic acids. In certain embodiments, the present invention provides a method of coarsely clarifying cell lysate from microorganisms that comprises: lysing the microorganisms under the normal atmospheric pressure to form a flocculent precipitate in the lysate, compressing the flocculent precipitate in the lysate by reducing or increasing the pressure of the atmosphere surrounding the lysate in relation to the normal atmospheric pressure to form a compressed flocculent phase and a liquid phase, and separating the two phases.

6 Claims, 2 Drawing Sheets

METHOD FOR COARSE PURIFICATION OF CELL DIGESTS FROM MICROORGANISMS

The present invention relates to a process for the coarse clarification of lysed cell material from microorganisms, particularly bacteria—such as for example *E.coli.*

Molecular-biological processes are gaining increasing importance in a range of fields, such as, for example, in the production of pharmaceuticals, in particular. In the recovery of so-called plasmid DNA the particular problem arises of obtaining the plasmid DNA in the purest form possible. In order to be able to produce plasmid DNA for example on a preparative scale, it is necessary to replicate the plasmids using so-called host cells. These are generally gram-positive or gram-negative bacteria—such as e.g. mutants of *E.coli.*

A particular problem is presented in this context by the removal of unwanted genomic DNA, RNA and endotoxins, which originate from the microorganisms used for the replication. As the above-mentioned nucleic acids belong to the same category of biomolecules, they also have certain physicochemical properties comparable to those of plasmid DNA and thus constitute a major problem in the purification or separation of the plasmid DNA.

Whereas the separation of the unwanted or contaminating nucleic acids and endotoxins is a problem which can be overcome on an analytical scale, up till now comparable success has only been achieved on a preparative scale at considerably greater expense. When solving problems of purification of this kind, in the majority of cases the technician is at pains to separate unwanted impurities at the earliest possible stage of the process so as to avoid the entrainment of the impurities.

The lysis of cells from microorganisms is the initial step in the isolation of purification of plasmid DNA from these microorganisms. After the lysis has been carried out—which is usually done using a lysis buffer such as e.g. SDS (sodium dodecyl sulphate) in the presence of sodium hydroxide—in addition to the individual cell constituents the fragments of the cell wall to which the genomic DNA is bound via membrane-associated proteins are also present in the reaction solution. However, this binding is very weak, which means that mechanical force is sufficient to undo these bonds. The genomic DNA thus released into the aqueous supernatant can then no longer be easily separated from the plasmid DNA or RNA in later purification steps.

In the production of cell lysates, flocculent precipitates are formed during the working up process after the neutralisation or acidification of the solution resulting from the basic lysis mentioned above—for example using potassium acetate solution. These precipitates consist of potassium dodecyl sulphate (PDS, the potassium salt of SDS) which is precipitated by addition to and denaturing of cell-wall-associated proteins together with the cell wall and the cell membranes and other cell constituents. Thus, the genomic DNA anchored to the cell wall is also bound in these complexes. In the case of smaller—for example analytical—preparations the separation of the PDS-protein-cell wall complex can be achieved by centrifugation, which simultaneously also substantially eliminates the genomic DNA.

With regard to so-called "high throughput" applications or preparations on a larger scale, separation of the flocculent precipitate from the supernatant by centrifugation or filtration is not advisable on account of the obstacles mentioned above or is beset by major problems. Thus, centrifugation e.g. in batches can only be applied to larger production runs to a very limited extent, while continuous centrifuging increases the content of genomic DNA released from the PDS precipitate in the aqueous supernatant.

During filtration, blockage and shearing problems arise on a preparative scale when the filter is charged with bacterial lysate containing flakes. In this way the content of genomic DNA in the filtrate would also seriously contaminate the plasmid phase. As a further disadvantage clogging of the filter is a frequent occurrence.

The aim of the present invention is thus primarily to provide a process for recovering plasmid DNA or RNA which can be used on a preparative scale and wherein the plasmid DNA or RNA can consequently be obtained in a form substantially free from genomic DNA and endotoxins.

A further aim of the present invention is to provide a process which is as simple and practical as possible which avoids the disadvantages known from the prior art.

The aims outlined above are achieved by carrying out cell lysis of biological material (microorganisms) in a method known per se from the prior art. The resulting reaction mixture is subjected to a change in pressure, i.e. an increase or reduction in pressure compared with normal pressure, preferably a pressure reduction.

The surprising advantage of this step is that due to the change in the pressure of the atmosphere surrounding the reaction mixture according to the invention the flakes float or sink, eventually resulting in a spatially highly compressed flocculent phase. The flocculent phase settles on the liquid phase and can easily be totally separated from the liquid phase. In the process proposed according to the invention the pressure of the atmosphere surrounding the reaction mixture is preferably adjusted to a value which is 200 to 1000 mbar lower than normal pressure (air pressure under normal conditions). Most preferably, the pressure is reduced to a level in the range from 300 to 800 mbar.

A similar effect is achieved if a pressure above ambient pressure is selected—preferably from 200 to 5000 mbar and most preferably from 200 to 2500 mbar above normal pressure. This measure also leads to the formation of a flocculent phase, although in this case the flocculent phase sinks, instead of floating on the liquid.

Thus, to summarise, the operating measure according to the invention has the following result:

1. The phase separation takes only a few minutes and no more than 30 to 180 minutes—even with larger volumes of 50 litres or more.
2. The phase separation leads to a spatially highly compressed flocculent phase, as a result of which the proportion by volume of the aqueous phase containing the product increases at the same time.

These surprising effects have the following particular advantages:

1. No PDS flakes are exposed to shear forces during subsequent filtration or centrifugation steps.
2. When larger amounts are used the process times for the clarification of cell lysates—such as e.g. in the production of plasmid DNA using *E.coli*—are significantly reduced as the filtration units used no longer clog up, or clog up later, and higher flow rates can be selected. The yield can be increased by about 10 to 30% using the process according to the invention (as the phase containing the flocculate is significantly more compressed than the corresponding phase which can be prepared under normal pressure conditions).
3. In automated high throughput applications—or applications on the so-called bench scale—by using the process according to the invention, time-consuming centrifugation steps can be dispensed with or the filtration can be speeded up by the preliminary separation of the flocculent phase from the aqueous phase, which can be carried out according to the invention, and the risk of blockage of the filter membrane, for example, can be significantly reduced. This technology is also suitable for integration into fully automated high throughput applications.

4. The compacting of the flocculate which can be achieved according to the invention is carried out with extremely low shear forces, thus minimising the risk of detachment of the genomic DNA and endotoxins from the fragments of the cell wall, as already mentioned.

This latter effect in particular has proved exceptionally beneficial, as it is possible using the process according to the invention to obtain a plasmid DNA or RNA which is contaminated with negligibly small amounts of genomic DNA and endotoxins. Similar advantageous effects were hitherto only known from the prior art for processes in which separation was carried out by sedimentation, for example; However, it is obvious to the skilled man that separation by sedimentation in this way embodies exceptionally time-consuming procedures which—in the event of incomplete phase separation—lead to an unsatisfactory result and cannot be scaled up infinitely for industrial production. For treating larger quantities this process is therefore without doubt ruled out as a serious alternative in any case.

Another advantage of the process according to the invention is that during subsequent filtration steps the filters take considerably longer to clog up than when non-clarified bacterial lysate is used.

In order to carry out the recovery of plasmid DNA and RNA from cells of microorganisms according to the invention the starting material is subjected to alkaline lysis which is known from the prior art.

After any necessary neutralisation of the mixture resulting from the lysis step a vacuum is applied with a pressure which is 200 to 1000 mbar lower than normal pressure (air pressure). It is particularly preferable to reduce the pressure by an amount ranging from 300 to 800 mbar.

In an alternative embodiment an ambient pressure above normal pressure is selected, preferably in the range from 200 to 5000 mbar and most preferably in the range from 200 to 2500 mbar above normal pressure.

Figure 1B:
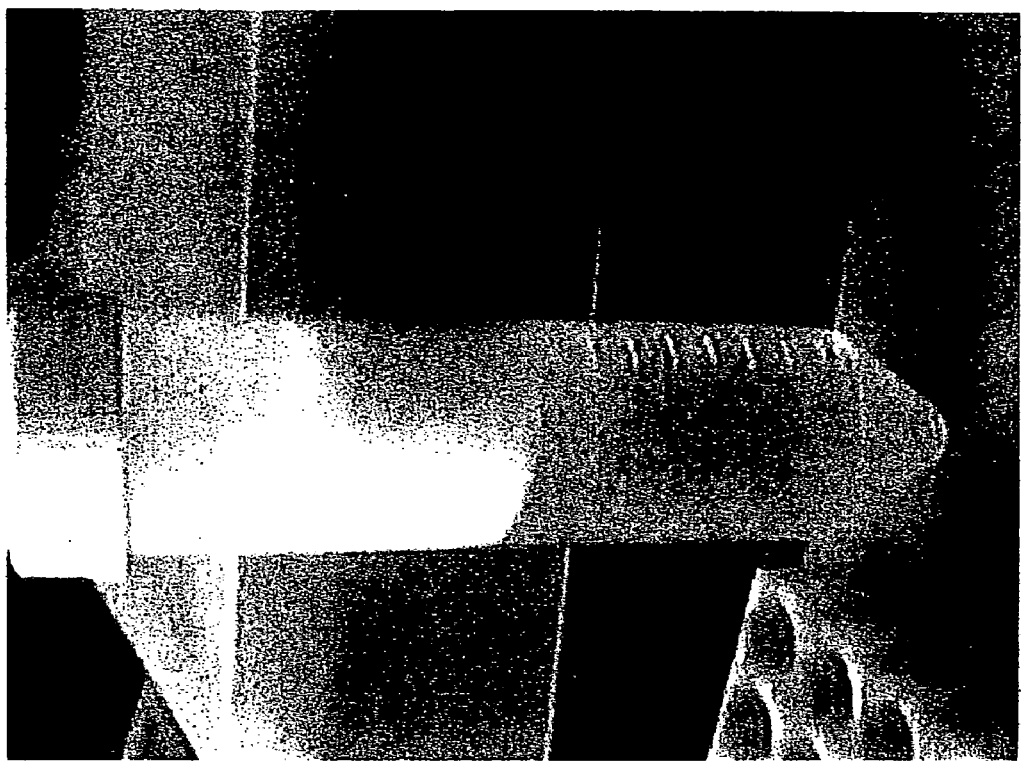
FIG. 1 shows a reaction mixture before the process according to the invention (FIG. 1A) and after the application of a vacuum (FIG. 1B) on the 50 ml scale.
Figure 1A:
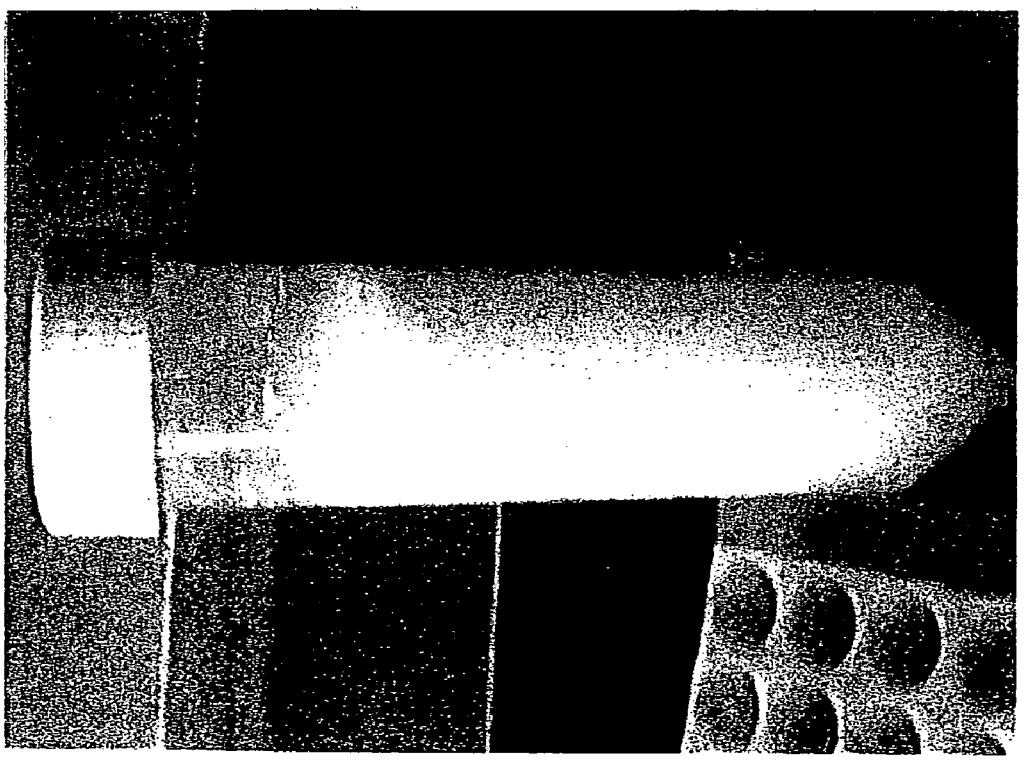
Figure 2B:
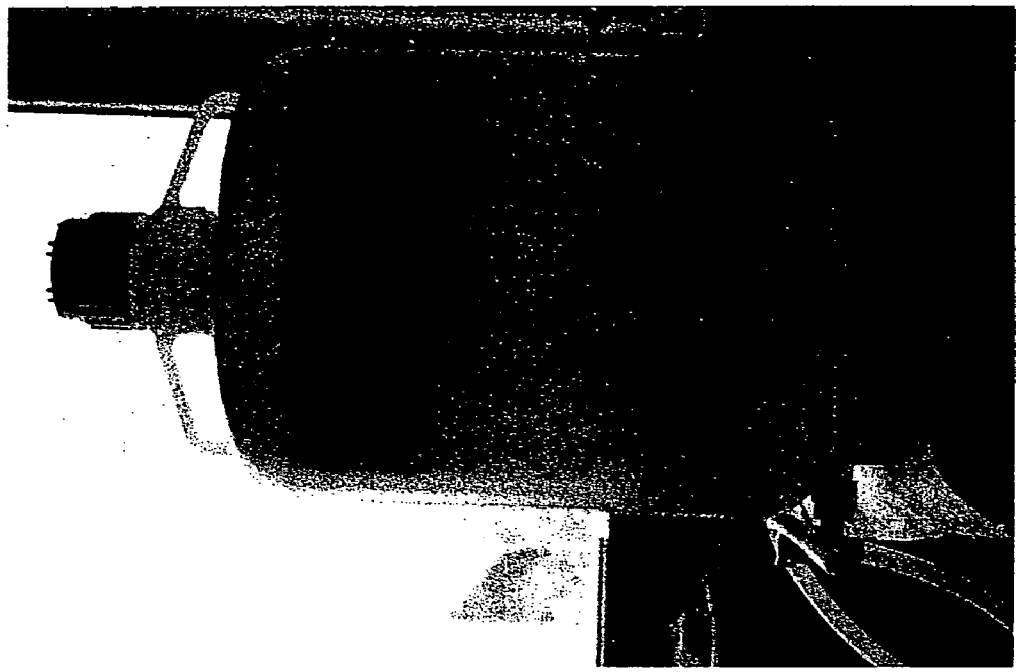
FIG. 2 shows a lysis mixture according to Example 3 on a 50 litre scale—as in FIG. 1—before the application of a vacuum (FIG. 2A) and after the process according to the invention has been carried out (FIG. 2B).
Figure 2A:
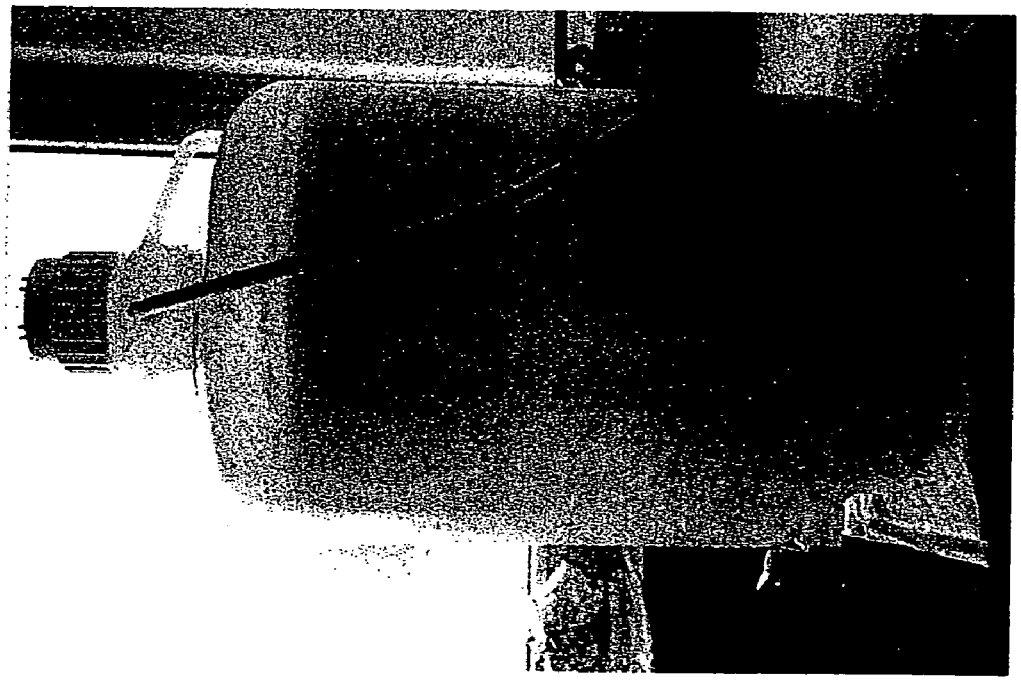

The Examples that follow are intended to illustrate the invention:

EXAMPLE 1

68 g of frozen pUC19 biomass are thawed in a glass beaker and in one litre of a standard commercial resuspension buffer (P1 buffer made by Messrs. QIAGEN, D-40724 Hilden) and homogenised by shaking. Then 1 litre of a standard commercial cell lysis buffer is added (P2 buffer made by Messrs. QIAGEN, D-40724 Hilden) and the biomass is subjected to lysis. The lysis process is also assisted by shaking, for example. The incubation time for this step is at least 5 minutes. The lysate thus obtained is transferred into a reaction vessel of a suitable size for clarification (volume about 5 litres) and mixed with one litre of an ice-cooled standard commercial neutralisation buffer (P3 buffer made by Messrs. QIAGEN, D-40724 Hilden). Then a light vacuum of about 500 mbar is applied to the reaction vessel over a period of about 3 minutes. The solid constituents are observed to float up immediately. The clarified lysate in the lower phase is free from solid constituents (according to visual inspection) and can be isolated or processed further.

EXAMPLE 2

1 g of frozen pQ73 biomass is thawed and resuspended in 15 ml of a standard commercial resuspension buffer (P1 buffer made by Messrs. QIAGEN, D-40724 Hilden). Then 15 ml of a standard commercial cell lysis buffer (P2 buffer made by Messrs. QIAGEN, D-40724 Hilden) are added and the biomass is subjected to lysis and incubated on ice for a period of about 5 minutes. The resulting lysate is mixed with 15 ml of an ice-cooled standard commercial neutralisation buffer (P3 buffer made by Messrs. QIAGEN, D-40724 Hilden) and shaken. The reaction vessel is transferred into a desiccator and exposed to a vacuum of 0.7 bar for a period of about 7 minutes. Again, the solid constituents are observed to float up immediately.

EXAMPLE 3

100 g of harvested biomass from a 200 litre fermentation with *E.coli*, which was transformed with the plasmid pQ81, are thawed in 500 ml of a standard commercial resuspension buffer (P1 buffer made by Messrs. QIAGEN, D-40724 Hilden), resuspended with a magnetic stirring rod and mixed with 1000 ml of resuspension buffer (P1 buffer made by Messrs. QIAGEN, D-40724 Hilden) in a 5 litre flask. Then 1.5 litre of cell lysis buffer (P2 buffer made by Messrs. QIAGEN, D-40724 Hilden) are added and the suspension is mixed by inverting it several times. It is then incubated for 10 minutes at ambient temperature while the bacteria lyse. After the incubation 1.5 litre are added at 4–8° C. of an ice-cooled standard commercial neutralisation buffer (P3 buffer made by Messrs. QIAGEN, D-40724 Hilden) and again mixed by inverting, whereupon the potassium dodecyl sulphate precipitate (PDS precipitate) settles out.

The cell lysates thus formed (10×4.5 litre) are carefully decanted into a 50 litre clarifying flask. Then the internal pressure of the flask is reduced to an ambient pressure of 600 mbar (corresponding to 400 mbar below normal pressure). The vacuum is maintained until all the flakes have floated to the surface. The process takes about 5–10 minutes. Then the vacuum is removed and the clear cell lysate is let out of the clarifying flask from the bottom until the PDS phase flocculating at the top reaches the lower outlet tap. The liquid phase thus obtained is free from visible flakes, according to visual inspection.

EXAMPLE 4

1 litre of LB Miller is inoculated with the *E.coli* strain DH5 alpha RCB and incubated for about 12 h at a temperature of 37° C. in a shaker. Then the bacteria are centrifuged off. The pellet thus obtained is resuspended in 75 ml of a standard commercial resuspension buffer without RNase (e.g. P1 buffer of Messrs QIAGEN, D-40724 Hilden) and added with 75 ml of a standard commercial lysis buffer (e.g.

P2 buffer of Messrs QIAGEN, D-40724 Hilden) and mixed by shaking carefully. After the lysis of the bacteria, the preparation is neutralised with 75 ml of a standard commercial neutralisation puffer (e.g. P3 buffer made by Messrs QIAGEN, D-40724 Hilden). The reaction mixture is exposed to a pressure 700 mbar below normal pressure for a period of 2 minutes. The cell debris is immediately separated off, forming a compact plug on the surface of the liquid.

Subsequent purification, e.g. by column chromatography, comprising the steps of binding the RNA to the matrix, washing the bound RNA with a suitable washing buffer and then eluting with subsequent precipitation of the RNA from the eluate with isopropanol, yields the RNA in a total yield of 720 µg of good quality RNA.

The invention claimed is:

1. A method of coarsely clarifying cell lysate from microorganisms comprising sequentially:
   i. lysing the microorganisms under the normal atmospheric pressure, wherein a flocculent precipitate is formed in the lysate;
   ii. compressing the flocculent precipitate in the lysate by reducing or increasing the pressure of the atmosphere surrounding the lysate in relation to the normal atmospheric pressure, wherein a highly compressed flocculent phase and a liquid phase are formed in the lysate; and
   iii. separating the two phases.

2. The method according to claim 1, wherein the microorganism is a bacterium.

3. The method according to claim 1 or 2, wherein the pressure of the atmosphere surrounding the lysate is adjusted to a level which is 200 to 1000 mbar lower than the normal atmospheric pressure.

4. The method according to claim 3, wherein the pressure of the atmosphere surrounding the lysate is adjusted to a level which is 300 to 800 mbar lower than the normal atmospheric pressure.

5. The method according to claim 1 or 2, wherein the pressure of the atmosphere surrounding the lysate is adjusted to a level which is 200 to 5000 mbar higher than the normal atmospheric pressure.

6. The method according to claim 5, wherein the pressure of the atmosphere surrounding the lysate is adjusted to a level which is 500 to 2500 mbar higher than the normal atmospheric pressure.

* * * * *